(12) United States Patent
Samuelsen et al.

(10) Patent No.: US 6,482,491 B1
(45) Date of Patent: Nov. 19, 2002

(54) ARTICLE HAVING A SURFACE SHOWING ADHESIVE PROPERTIES

(75) Inventors: Peter Boman Samuelsen, Rungsted Kyst (DK); Anders Christian Nielsen, Koebenhavn N (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/581,546

(22) PCT Filed: Jan. 26, 1999

(86) PCT No.: PCT/DK99/00037
§ 371 (c)(1),
(2), (4) Date: Aug. 21, 2000

(87) PCT Pub. No.: WO99/38929
PCT Pub. Date: Aug. 5, 1999

(30) Foreign Application Priority Data

Jan. 30, 1998 (DK) .............................. 01281/98

(51) Int. Cl.⁷ .............................. C09J 7/02; B32B 3/26; A61F 13/02; A61L 15/58
(52) U.S. Cl. .................... 428/40.1; 428/41.7; 428/202; 442/149; 442/151; 424/448; 424/449
(58) Field of Search .............................. 428/40.1, 41.7, 428/42.3, 41.9, 198, 202; 424/448, 449; 442/149, 150, 151

(56) References Cited

U.S. PATENT DOCUMENTS

| 3,419,006 A | | 12/1968 | King | 128/268 |
|---|---|---|---|---|
| 3,438,371 A | * | 4/1969 | Fischer et al. | 128/156 |
| 3,763,858 A | | 10/1973 | Buese | 128/156 |
| 3,972,328 A | | 8/1976 | Chen | 128/156 |
| 4,367,732 A | | 1/1983 | Poulsen et al. | 128/156 |
| 4,538,603 A | | 9/1985 | Pawelchak et al. | 128/156 |
| 4,552,138 A | | 11/1985 | Hofeditz et al. | 128/156 |
| 4,699,792 A | * | 10/1987 | Nick et al. | 424/446 |
| 4,711,781 A | | 12/1987 | Nick et al. | 424/446 |
| 4,867,748 A | | 9/1989 | Samuelsen | 604/336 |
| 4,990,144 A | * | 2/1991 | Blott | 604/304 |
| 5,051,259 A | | 9/1991 | Olsen et al. | 424/443 |
| 5,133,821 A | | 7/1992 | Jensen | 156/245 |
| 5,714,225 A | | 2/1998 | Hansen et al. | 428/114 |
| 5,840,327 A | * | 11/1998 | Gale et al. | 424/448 |

FOREIGN PATENT DOCUMENTS

| EP | 0 117 027 | 8/1984 |
|---|---|---|
| EP | 0 256 893 | 2/1988 |
| EP | 0 264 299 | 4/1988 |
| EP | 0 272 149 | 6/1988 |
| EP | 0 415 183 | 8/1990 |
| GB | 1 280 631 | 7/1972 |
| GB | 1 586 182 | 8/1981 |
| WO | WO88/06894 | 9/1988 |
| WO | WO93/02717 | 2/1993 |

* cited by examiner

Primary Examiner—Daniel Zirker
(74) Attorney, Agent, or Firm—Jacobson Holman PLLC

(57) ABSTRACT

An article having a surface showing adhesive properties and a cover layer for protecting the adhesive surface wherein a further component is located in indentations in the surface f the cover layer facing the adhesive surface without being in direct contact with the adhesive surface enables a grading of the adhesive properties of the article.

11 Claims, 1 Drawing Sheet

ARTICLE HAVING A SURFACE SHOWING ADHESIVE PROPERTIES

FIELD OF THE INVENTION

The present invention relates to an article having a surface showing adhesive properties, a method of producing such an article, a method of grading the adhesive properties of an article having a surface showing adhesive properties, and the use of a cover layer comprising indentations for the production of an article having a surface showing adhesive properties wherein a further component is located between the cover layer and the adhesive surface without being in direct contact with the adhesive surface.

BACKGROUND OF THE INVENTION

Pressure sensitive adhesives intended for medical use and in particular for adhesion to the skin of human beings must meet much more complex and varying conditions as compared to adhesives intended to be used on well defined surfaces. This is to be ascribed inter alia to the variability of the surface structure and the surface film of the skin. The variation reflects inter alia age and races but also influence from the local climate is vital for the behaviour of the skin. Furthermore, there may be specific requirements to adhesives to be used for certain applications relating to treatment human beings having diseases or handicaps. For instance, adhesives used for carrying ostomy bags or used for treatment of a skin ulcer will be affected not only by the normal variations differences of the skin but also by the secretions from the stoma or from the wound. Thus, there is a need of an option of a local and individual grading of the adhesive properties of an adhesive to obtain a better and more reliable performance.

It is known to provide adhesive surfaces with discrete areas comprising a further component. Thus, U.S. Pat. No. 4,711,781 to Nick et al. discloses a medicinal self-adhesive plaster which comprises a continuous adhesive coating on one surface of a carrier web, a plurality of non-permeable, separating film elements spaced from each other on the surface of the adhesive coating and a plurality of active ingredient elements containing a medication, each disposed on the surface of one of the separating film elements whereby the medicated active ingredient is isolated from the adhesive composition.

It is an object of the present invention is to overcome the problems related to the complex demands related to effectively control the properties of a pressure sensitive adhesive..

BRIEF DESCRIPTION OF THE INVENTION

The present invention relates to an article having a surface showing adhesive properties which may be adapted to the specific needs of the user.

Furthermore, the invention relates to a method of producing an article having a surface showing adhesive properties which may be adapted to the specific needs of the user, to a method of grading the adhesive properties of an article having a surface showing adhesive properties, and to the use of a cover layer comprising indentations for the production of an article having a surface showing adhesive properties wherein a further component is located between the cover layer and the adhesive surface without being in direct contact with the adhesive surface.

BRIEF DESCRIPTION OF THE DRAWINGS

The invention is disclosed more in detail with reference to the drawings in which.

DETAILED DESCRIPTION OF THE INVENTION

Figure 1:
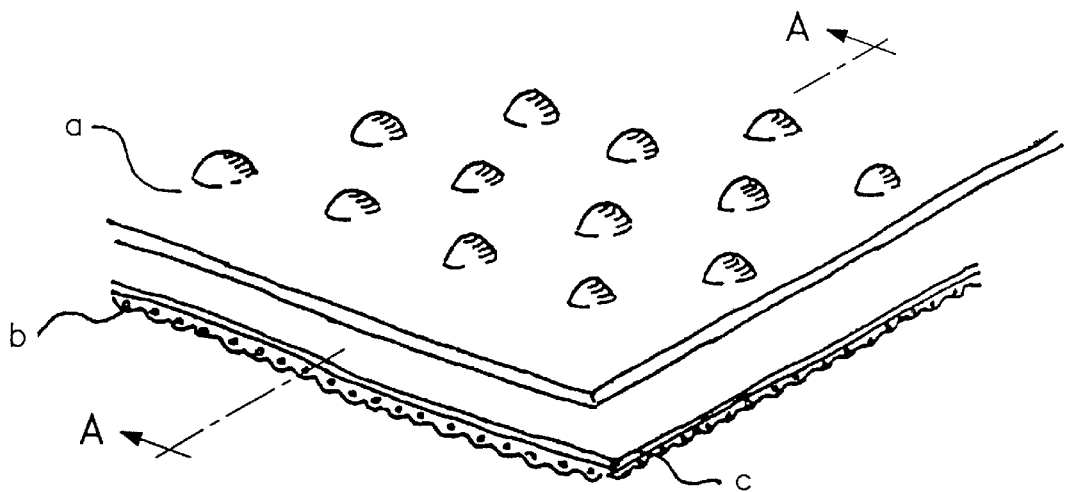
FIG. 1 shows an embodiment of an article according to the invention.
Figure 2:
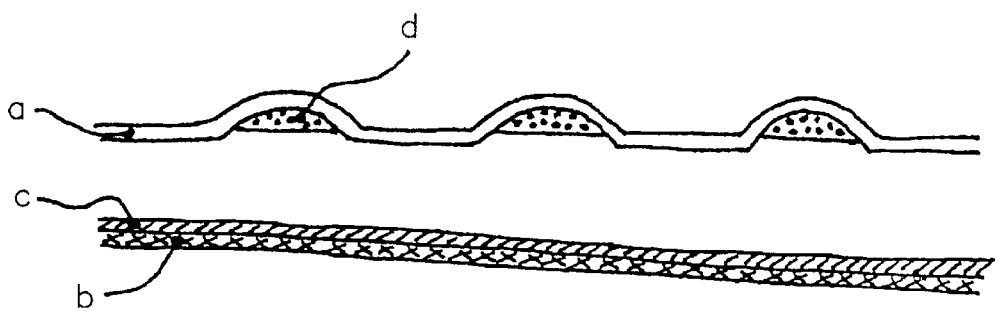
FIG. 2 shows a sectional partially exploded view along the line A—A in FIG. 1.

The present invention relates to an article having a surface showing adhesive properties and a cover layer for protecting the adhesive surface wherein a further component is located in indentations in the surface of the cover layer facing the adhesive surface without being in direct contact with the adhesive surface The articles of the invention are preferably having an essentially two dimensional surface showing adhesive properties and may be in the form of a sheet or a disc. The PSA is preferably placed on a backing in the form of a film of a plastics material or the like.

The type and form of the indentations are not critical and indentations used according to the invention may e.g. be folds, grooves, ridges, bulges, bosses, bumps, lumps or bunches, or combinations thereof.

It is preferred that the amount of further component located in the indentations formed in the cover layer is below the volume of the indentations and that the further component is placed within the indentations without being in contact with the rim thereof. This preferred embodiment of the invention renders it possible to apply the further component between the adhesive surface and the cover layer without contact with the adhesive surface.

The further component may be in the form of a dot or drop or plate or disc placed in the indentations. The further component may be brought into contact with the adhesive surface, if desired, simply by pressing the cover layer against the adhesive surface using e.g. a finger which enables a controlled manner of applying the further component to the desired fraction of the adhesive surface.

Thus, it is possible, if desired, to control e.g. the adhesiveness of a surface of an article by providing a part of the adhesive surface of the article having such a surface with a second component having a different adhesiveness when applying the article. Hence, it is possible to increase the adhesiveness by applying a second component in the form of an adhesive having a stronger binding force to the substrate to which the article is to be applied or to reduce the adhesiveness by applying a second component having a weaker binding force to a desired part of the surface of the substrate. Furthermore, it is possible to graduate the adhesiveness, e.g. so as to increase the adhesiveness along the rim of the article when applying the same to an area in which it may be subject to increased forces due to for example friction in order to reduce the risk of "rolling-up" the edge of the article (separation of the article form the skin). This may be of interest when applying e.g. medical dressings to parts of the body exposed to frictional forces.

It is also possible, at the descretion of the person applying the article, to decide whether or not to change the adhesive properties thereof immediately before the application by simply deciding whether to elicit the application of the second component to the adhesive surface.

Such a control of the adhesive properties of a surface having an adhesive coating is neither disclosed nor indicated in U.S. Pat. No. 4,711,781.

It is preferred that the indentations form a pattern which may provide for a more uniform distribution over the adhesive surface and enabling a simple way of controlling the fraction of a surface to which it is desired to apply the second component.

The invention may be used in many technical fields using any appropriate adhesive. According to the invention it is preferred, and has not been proposed until now, to grade adhesive properties of medical adhesives for use on human skin.

The adhesive properties of the articles according to the invention preferably are provided by a pressure sensitive adhesive (PSA).

The PSA and the further component may be constituted by a wide range of different types of adhesives for instance the hydrocolloid type (thick), acrylic types, and types derived from PIB, polyurethanes, EVA-compounds, APAO'S, silicones, polyvinyl ether etc. Such adhesive materials may be used for both the first adhesive and for the modifying component and the types may be chosen freely according to properties irrespectively that there may be lack of compatibility or there may be lack of stability as the product will be formed in situ and the application period in most instances will not be more than 14 days for medical applications.

The medical adhesive may e.g. be an adhesive comprising hydrocolloids or other moisture absorbing constituents for prolonging the time of use. The adhesive may suitably be of the type disclosed in those disclosed in GB patent specification No. 1 280 631, in DK patent specifications Nos. 127,578, 148,408, 154,806, 147,226 and 154,747, in EP published application Nos. 0 097 846 and 0 415 183, in SE published application No. 365,410, in WO publication No. 88/06894, in U.S. Pat. No. 4,867,748, and in NO published application No. 157,686. Especially preferred are the adhesives disclosed in U.S. Pat. Nos. 4,367,732 and 5,051,259 and DK patent specification No. 169,711.

The article according to the invention is preferably a wound dressing, a dressing for treatment of skin disorders, an ostomy appliance, an incontinence device, a breast prosthesis.

A dressing or ostomy appliance of the invention preferably has bevelled edges in order to reduce the risk of "rolling-up" the edge of the dressing or ostomy appliance reducing the wear-time and thus disturbing and prolonging the healing of wounds or e.g. cracks normally healing slowly on tips of fingers or toes due to physical stress. A bevelling may be carried out discontinuously or continuously in a manner known per se e.g. as disclosed in EP patent No. 0 264 299 or in U.S. Pat. No. 5,133,821.

The adhesive may be produced in any manner known per se, e.g. coating from solvent, emulsion or hot melt on release liners, films or webs of different nature.

The adhesive surface may be the free surface of an adhesive layer placed on a water impervious backing layer or film which may be of any suitable material known per se for use in the preparation of wound dressings e.g. a foam, a non-woven layer or a polyurethane, polyethylene, polyester or polyamide film. The load of adhesive is suitably the same load of adhesive as is conventionally used for the production of wound dressings or ostomy appliances.

The adhesive may impart further specific properties like conductivity or insulation.

The material for modifying the adhesive surface may be adherent or non adherent, be gel like, be absorbent, contain pharmaceutical agents, contain specific bonding or moisturising or soothing agents.

The modifying component or further agent may thus be an adhesive with higher or lower adhesiveness than the first adhesive depending on the desired modification of the properties. It may also be adhesives having another adhesive nature for instance a hydrophilic adhesive to be transferred to a hydrophobic adhesive or vice versa. Furthermore, the material may impart quite different properties such as antibacterial or antifungal properties to the adhesive or transfer indicators of different sort like pH, conductive or thermal indicators. Still further, the further agent may comprise other pharmaceutically active compounds for instance for enhancing wound healing or treatment of e.g. psoriasis arthritis or other skin diseases.

Thus, an article according to the invention may be a dressing in the form of a corn pad or a dressing for treatment of warts, callus or psoriasis.

On the adhesive sheet or disc is affixed a cover layer or release liner, preferably a silicone based release liner.

The cover layer or release liner used in accordance with the invention is characterised in being deformable, preferably mouldable by thermoforming. The protective cover or release liner will typically be siliconized thermoplastic on for example polyolefins such as polyethylene, polypropylene or the like. Furthermore, other types of films mouldable using stress and/or elevated temperatures may be utilised for the purpose. Examples are thermoplastic polyurethanes, polyesters, polyamides, polyvinylacetate and the like. The cover film or sheet may be moulded by injection moulding for instance in form of a silicone or other elastic and siliconized material to the final shape with e.g. grooves.

When indentations are formed into the release liner, only the part of it not being subjected to moulding will be in contact with the adhesive surface when laminated together when using a gentle lamination force. For the intended use according to the invention, the release liner must still be sufficiently deformable to enable establishment of a contact of the area of the release liner with the adhesive surface when a firm pressure is applied to the opposite side of the release liner, for instance with the pressure from a finger which implies that the further component is brought into contact with the adhesive surface modifying a part of or the full surface thereof before utilising the adhesive properties of the surface, e.g. for adhering a medical device such as an ostomy appliance or a wound dressing or for adhering other articles such as a wig to human skin.

In a second aspect, the invention relates to a method of producing an article having a surface showing adhesive properties and a cover layer for protecting the adhesive surface wherein a further component is located in indentations in the surface of the cover layer facing the adhesive surface without being in direct contact with the adhesive surface wherein one or more indentations is formed in the cover layer, the further component is placed in the indentations, and the cover layer is laminated with the surface showing adhesive properties using a gentle lamination force not bringing the further component into contact with the adhesive surface.

The cover layer or release liner comprising material to be transferred to the adhesive may be produced in various ways known per se, e.g. by embossment or drawing or similar techniques.

A preferred method is starting from a flat thermoplastic release liner. Indentations or grooves may be processed into said release liner by stress deformation at ambient temperature but more preferable by permanent deformation due to moulding at elevated temperatures. The principles of thermo forming, e.g. vaucuum forming, may generally be used and additionally, pressure may be applied to one side of the release liner material according to common practice known to the skilled person. The pattern and size of the grooves or embossments or the like in the release liner may be selected according to the specific demand in use.

In each of the individual indentations an adhesive modifying material is applied in a manner known per se. One way of application is by printing for instance with tampon print or precision flexoprint. Another way of filling the indentations with modifying material is dosing this volumetrically from nozzles. The latter method will be advantageous in case of transferring of greater amounts of material to the adhesive to be modified.

The most preferred method will be to carry out both operations in one step i.e. both moulding the release liner forming the specified indentations and at the same time dosing the modifying material into the indentations. This can for instance be achieved by use of a printing roll in which the print transfer areas are used for the deformation of e.g. grooves in the release liner. Preferably, the release liner is preheated to a temperature suitable for easy moulding and at the same time easy transfer of the printing material, preferably using rollers for printing e.g. equivalent to the principles for flexo or tampon printing. Preferably one roller is cooled in order to "freeze" the grooves formed and filled with the modifying material in order to ensure that the modifying material does not fill the grooves completely and appear at the surface of the base plane. In a similar way a roller equipped with nozzles for both moulding the release liner forming e.g. grooves and for transfer of material for modification of the first adhesive is used. In the alternative, the indentations may be produced after applying the adhesive modifying second component at the intended site of the intendations.

In a third aspect, the invention relates to a method of grading the adhesive properties of an article having a surface showing adhesive properties and a cover layer for protecting the adhesive surface wherein a further component is located in indentations in the surface of the cover layer facing the adhesive surface without being in direct contact with the adhesive surface, wherein the further component is brought into contact with a fraction of the surface showing adhesive properties by pressing the cover layer against the surface showing adhesive properties bringing the further component into contact with the surface before removing the cover layer from the adhesive surface and applying the article.

The pressing for modifying the properties of the adhesive surface of a wound dressing or an ostomy appliance or the like may preferably be performed manually using e.g. a finger.

In a fourth aspect, the invention relates to the use of a cover layer comprising indentations for the production of an article having a surface showing adhesive properties and a cover layer for protecting the adhesive surface in which cover layer a further component is located in the indentations in the surface of the cover layer facing the adhesive surface without being in direct contact with the adhesive surface.

In a fifth aspect, the invention relates to the use of a cover layer comprising indentations for the production of a wound dressing, a dressing for treatment of skin disorders, an ostomy appliance, an incontinence device, a breast prosthesis or other articles to be adhered to human skin, e.g. a wig or the like, having a surface showing adhesive properties and a cover layer for protecting the adhesive surface wherein a further component is located in indentations in the surface of the cover layer facing the adhesive surface without being in direct contact with the adhesive surface.

In a further aspect, the invention relates to a method for providing a surface of an article with a further component modifying the properties of said surface of said article by bringing said surface into contact with a cover layer having indentations in the first surface thereof to contact the surface of the article to be modified, said cover layer being provided with the further component placed in the indentations without being in contact with the rim thereof and said cover layer being sufficiently deformable to enable establishment of a contact between the surface of the article to be modified and the further component by pressing at the top of the indentions from the second surface of the cover layer not in contact with the article and pressing at a desired fraction of the second surface to transfer the further component to the surface of the article.

The further component may be any of the abovememtioned. It is also considered an embodiment of the invention to apply a pattern of an adhesive to the surface of an article not being adhesive to render the surface adhesive.

An adhesive is chosen according to the use of the article and may be any adhesive being suitable for the intended use, e.g. a medical adhesive for articles to be adhered to the skin.

DETAILED DESCRIPTION OF THE DRAWINGS

The invention is disclosed more in detail with reference to the drawings showing embodiments of the invention.

Reference is made to FIG. 1 showing an embodiment of an article according to the invention comprising a backing layer or film comprising a nonwoven material b, an adhesive layer c and a cover layer or release liner a having embossments in the form of bulges, bosses, bumps, lumps or bunches. In the partially sectional exploded view along the line A—A in FIG. 1 is seen that the further component d is located in the tops of the bulges, bosses, bumps, lumps or bunches without contact with the adhesive layer when laminated using a gentle pressure.

Figure 3:
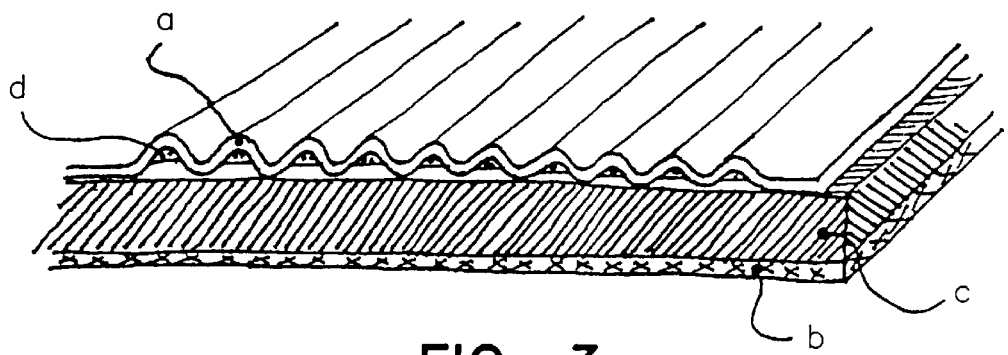
FIG. 3 shows a sectional view of another embodiment of an article according to the invention.

In FIG. 3 is shown a sectional view of another embodiment of an article according to the invention comprising a release liner having folds, grooves or, ridges in which the further component is placed.

In each of the grooves one or more adhesive modifying materials may be positioned according as indicated above. The modifying materials may if desired be transferred to the surface of the first adhesive when the grooves are pressed upon as described above.

The invention is explained more in detail in the below example showing modification of the adhesion of an embodiment of a dressing according to the invention.

EXAMPLE

A wound dressing according to the invention was prepared using a plate of a hydrocolloid adhesive having an peel adhesion of 18,4 N/25 mm at a speed of 304 mm/min at ambient temperature when removed from stainless steel, said plate having a thickness of 1000 microns and a polyester backing of a thickness of 35 microns. A 120 microns siliconised polyethylene release film was provided with grooves of a depth of 1 mm and a diameter of 5 mm and a distance between the grooves of 5 mm by deep drawing at 85 degrees C. and a vacuum of 0.1 atmosphere. Another adhesive material having a peel adhesion of 47 N/25 mm at a speed of 304 mm/min at ambient temperature when removed from stainless steel was placed evenly in the form of dots having a thickness of 10 microns in the grooves of the release film. The release film was then laminated to the plate of hydrocolloid adhesive with the side of the release film comprising the second adhesive facing the plate.

After pressing on the grooves revealed an adhesive composite having a mean peel adhesiveness of 30,8 N/25 mm. Thus, it is demonstrated that it is possible to control the adhesive properties og an adhesive surface by adding a second adhesive component to a fraction of the surface.

Thus, it is demonstrated that it is possible to control the adhesive properties of an adhesive surface according to the invention by adding to a fraction of the surface a second adhesive component having different adhesive properties.

What is claimed is:

1. An article having an adhesive surface and a cover layer for protecting the adhesive surface, said cover layer including a transferable component removably adhered to but not filling indentations in a surface of the cover layer facing the adhesive surface such that said component is not in direct contact with the adhesive surface but is separated therefrom by an empty space.

2. The article as claimed in claim 1, wherein the indentations form a pattern.

3. The article as claimed in claim 1, wherein the adhesive surface and said component are selected from the group consisting of medical pressure sensitive adhesives.

4. The article as claimed in claim 1, wherein the adhesive surface comprises a medical pressure sensitive adhesive, and said component contains one or more substances selected from the group consisting of an antifungal or antibacterial agent, an indicator such as pH, conductive or thermal indicators, and pharmaceutically active compounds such as compounds for enhancing wound healing or treatment of conditions such as psoriasis arthritis or other skin diseases.

5. The article as claimed in claim 1, said article being selected from the group consisting of a wound dressing, an article for treatment of skin disorders, an ostomy appliance, an incontinence device, a breast prosthesis and a means or strip for fixating of a medical device.

6. The article as claimed in claim 1, comprising a plurality of indentations formed by substantially parallel ridges in said cover layer.

7. The article as claimed in claim 1, wherein the adhesive surface and said component are selected from the group consisting of medical pressure sensitive adhesives, said component having a stronger binding force than said adhesive surface such that, when said component is transferred to at least a portion of said adhesive surface through pressure applied against said indentations, an adhesiveness of said portion of said adhesive surface is increased.

8. The article as claimed in claim 1, wherein the adhesive surface and said component are selected from the group consisting of medical pressure sensitive adhesives, said adhesive surface having a stronger binding force than said component such that, when said component is transferred to at least a portion of said adhesive surface through pressure applied against said indentations, an adhesiveness of said portion of said adhesive surface is decreased.

9. A method of producing an article having an adhesive surface and a cover layer for protecting the adhesive surface comprising the steps of:

forming an indentation in a surface of said cover layer facing said adhesive layer;

placing a transferable component within said indentation such that said indentation is only partially filled;

laminating said cover layer with said adhesive layer using a level of pressure insufficient to bring said component into direct contact with said adhesive layer such that said cover layer may thereafter be removed from said adhesive layer without any transfer of said component from said cover layer to said adhesive layer.

10. A method of applying an article having an adhesive surface and a cover layer for protecting the adhesive surface, said cover layer having a transferable component removably adhered within each of a plurality of indentations in a surface of said cover layer facing said adhesive layer such that an empty space separates said components from said adhesive layer, comprising the steps of:

pressing said cover layer against said adhesive layer to bring at least one of said components into contact with at least a portion of said adhesive layer, said component adhering to said portion when brought into contact therewith;

removing said cover layer; and applying said adhesive layer, with said component adhered thereto, to skin.

11. The method as claimed in claim 10, wherein said plurality of indentations are spaced from one another and arranged in a pattern such that, by selectively pressing against a top of some of said plurality of indentations, but not all, variable degrees of adhesion against the skin to which said adhesive layer is applied are realized due to a presence or absence of said component upon different portions of said adhesive layer.

* * * * *